United States Patent [19]

Coggins et al.

[11] Patent Number: 4,955,906
[45] Date of Patent: Sep. 11, 1990

[54] MAMMARY PROSTHESIS INJECTOR

[76] Inventors: Peter R. Coggins, Suite B104-105, Greenville Center, Greenville, Del. 19807; Andrew L. Mitchell, 1880 Superfine La., Wilmington, Del. 19802; Paul Brothers, 112 Mill Brook Dr., Chadds Ford, Pa. 19317; William L. Muir, 1295 W. Old Philadelphia Rd., Northeast, Md. 21901

[21] Appl. No.: 296,252
[22] Filed: Jan. 12, 1989
[51] Int. Cl.$^5$ ............................................. A61F 2/12
[52] U.S. Cl. ........................................................ 623/8
[58] Field of Search .................... 623/8, 7, 10, 11; 128/330, 830, 831, 832, 833, 838, 840; 604/11, 12, 13, 14, 15, 16, 17, 18, 54, 55, 57, 59, 68; 221/260, 64

[56] References Cited

U.S. PATENT DOCUMENTS

| 977,004 | 11/1910 | Grimm | 604/59 |
|---|---|---|---|
| 1,086,277 | 2/1914 | Clark | 221/260 |
| 2,509,241 | 5/1950 | Mende | 604/11 |
| 2,754,822 | 7/1956 | Emelock | 604/59 |
| 4,035,850 | 7/1977 | Cresswall | 623/8 |
| 4,413,986 | 11/1983 | Jacobs | 604/14 |
| 4,610,659 | 9/1986 | Friese | 604/15 |

FOREIGN PATENT DOCUMENTS 0537440  11/1958  Italy .................................... 604/15

Primary Examiner—David J. Isabella
Attorney, Agent, or Firm—Sixbey, Friedman, Leedom & Ferguson

[57] ABSTRACT

The instant invention is directed to a mammary prosthesis injector. The injector comprises a hollow tube having an opening at one end thereof. A bag for holding the prosthesis and reducing friction between the tube and the prosthesis is located, in part, within the tube. A mechanism for pulling the bag from within the tube is slidably mounted on the exterior of the tube and engages the bag. The prosthesis, which is held within the bag which is within the tube, is ejected from the tube and through the opening when the pulling mechanism is slid along the exterior of the tube.

14 Claims, 6 Drawing Sheets

U.S. Patent    Sep. 11, 1990    Sheet 1 of 6    4,955,906
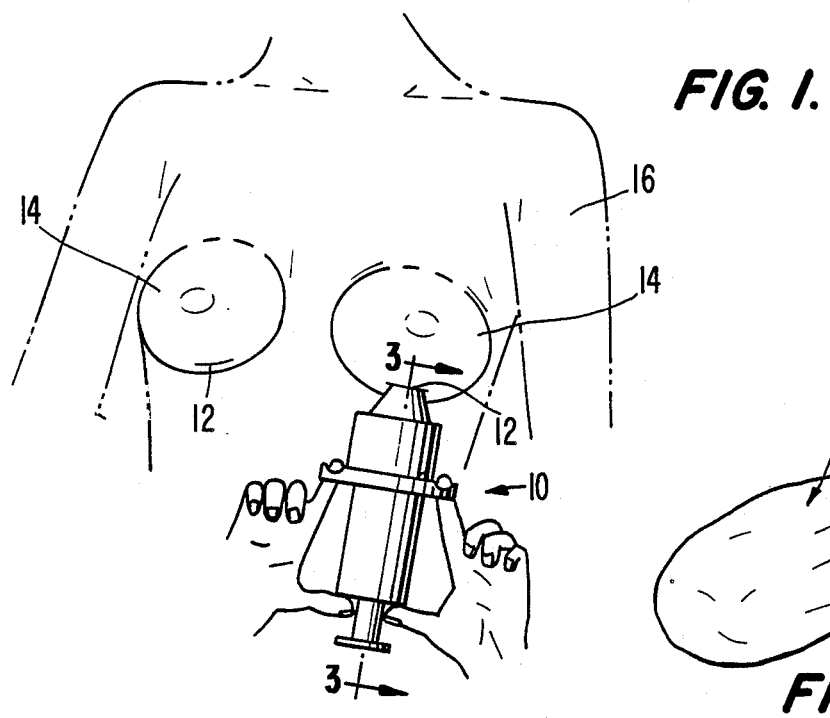
FIG. 1.
FIG. 2.
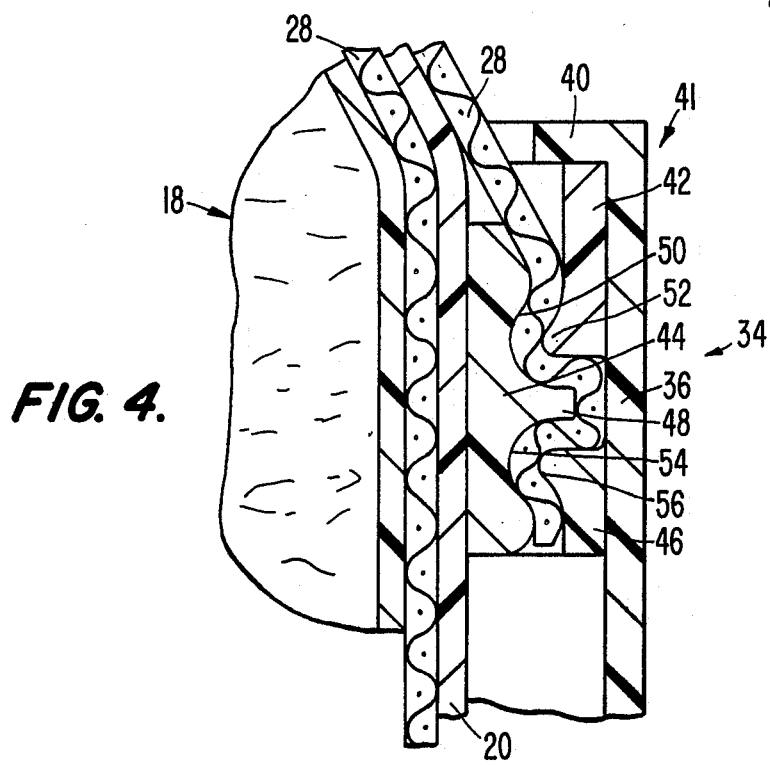
FIG. 4.

MAMMARY PROSTHESIS INJECTOR

FIELD OF THE INVENTION

The instant invention is directed to an apparatus and method for implanting a mammary prosthesis into a patient.

BACKGROUND OF THE INVENTION

Currently, there are an estimated 500,000 breast augmentations performed annually in the continental United States. These augmentations frequently utilize a mammary prosthesis consisting of Silastic ® bag filled with a liquid silicon. A new polyurethane foam prosthesis has, also, been recently introduced and is being used in a limited number of procedures.

The currently practiced method of implanting a mammary prosthesis is to manually push it through a small incision located at the fold at the lowermost base of the breast. The incision is smaller than the prosthesis, so insertion is difficult especially when coupled with fluids from the open incision. This manual insertion procedure is time consuming and frequently leads to capsule formation, an infection resulting from handling the prosthesis during implantation.

U.S. Pat. No. 4,035,850 to Cresswall is directed to a method and apparatus for inserting a mammary prosthesis into a patient. The apparatus comprises an inner opened mouth bag and an outer opened mouth bag which are sealed together, at their opened mouths, by ring member. Fluid fills the space between the two bags. The prosthesis is carried with the inner bag and ejected therefrom when the outer bag is squeezed.

SUMMARY OF THE INVENTION

The instant invention is directed to a mammary prosthesis injector. The injector comprises a hollow tube having an opening at one end thereof. A bag for holding the prosthesis and reducing friction between the tube and the prosthesis is located, in part, within the tube. A mechanism for pulling the bag from within the tube is slidably mounted on the exterior of the tube and engages the bag. The prosthesis, which is held within the bag which is within the tube, is ejected from the tube and through the opening when the pulling mechanism is slid along the exterior of the tube.

The instant injector is a great improvement over the prior practice of manually inserting mammary prosthesis into a patient. The instant injector also reduces the chance of foreign body contamination and bacterial infection caused by handling of the prosthesis during insertion because the prosthesis is transferred directly from the tube through the incision. The amount of time necessary to inject the prosthesis using the instant invention is also much less than the prior method of manually inserting the prosthesis through the incision.

DETAILED DESCRIPTION OF THE DRAWINGS

Figure 5:
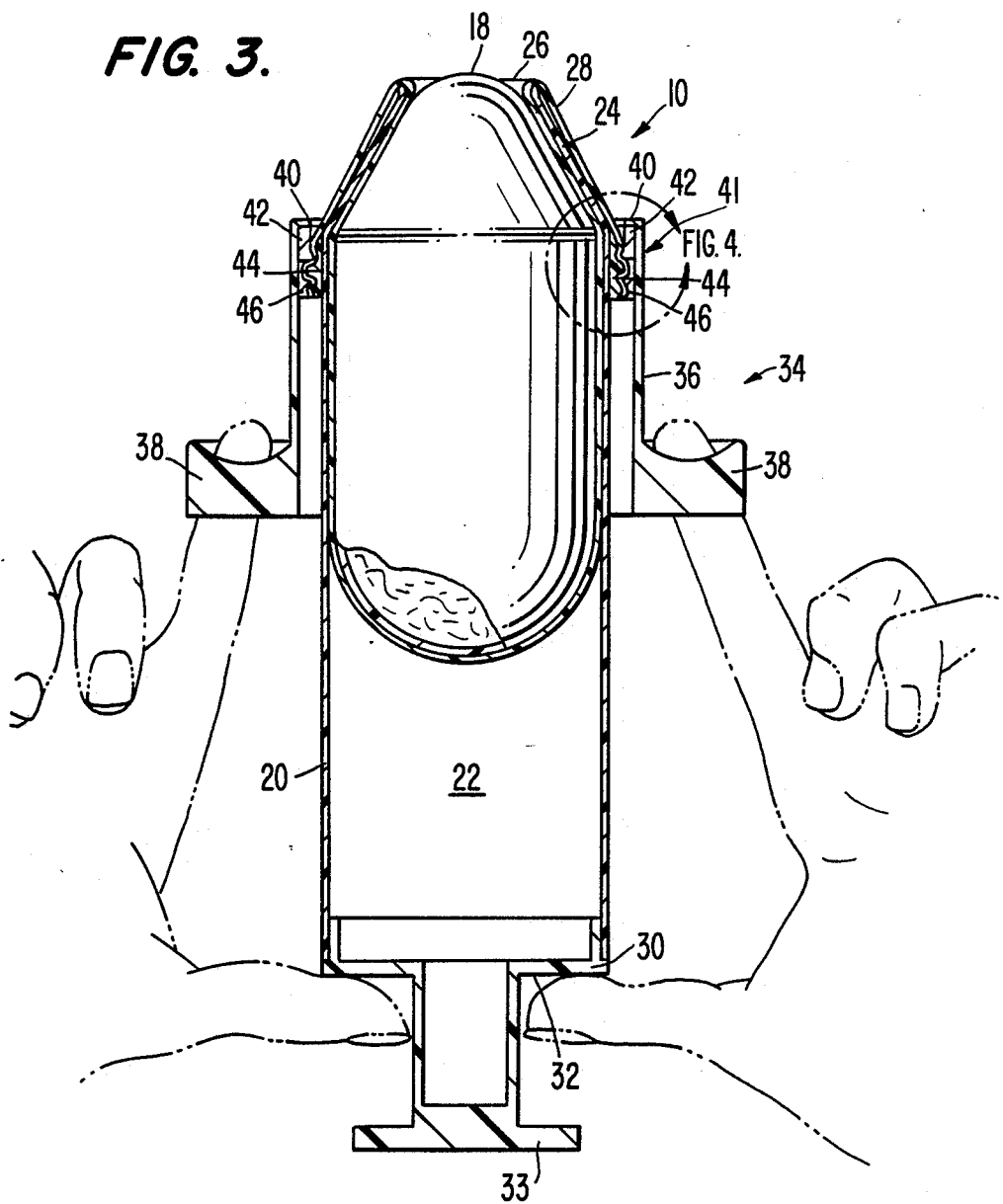

For the purpose of illustrating the invention, there is shown in the drawings a form which is presently preferred; it being understood, however, that this invention is not limited to the precise arrangements and instrumentalities shown.

Figure 6:
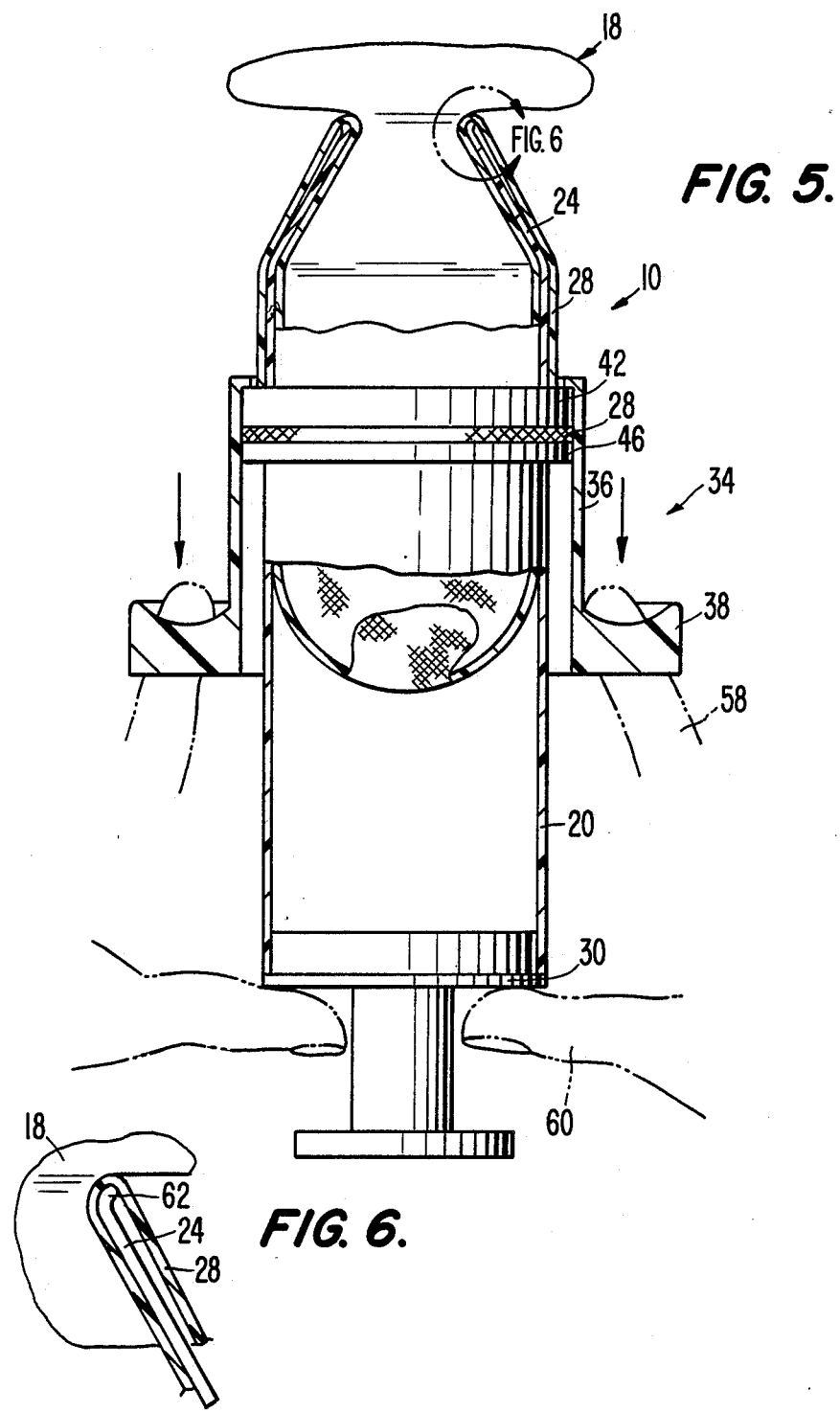
Figure 7:
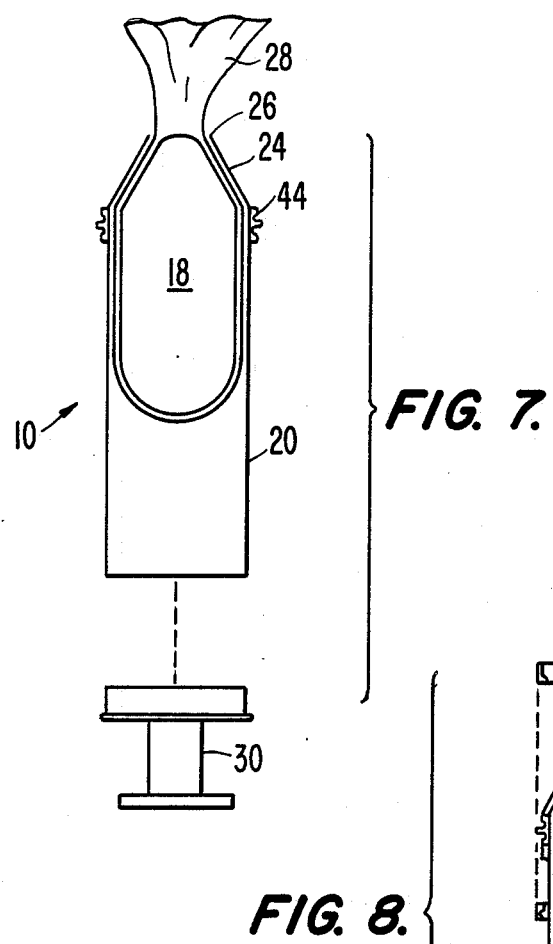
Figure 8:
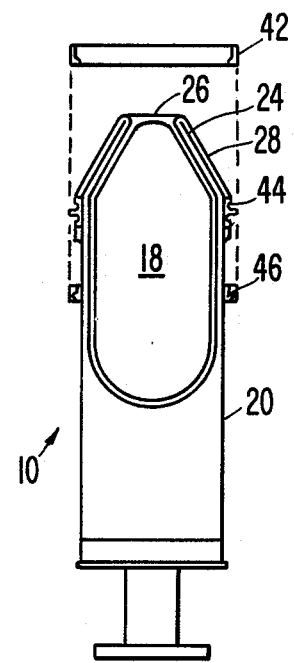
Figure 9:
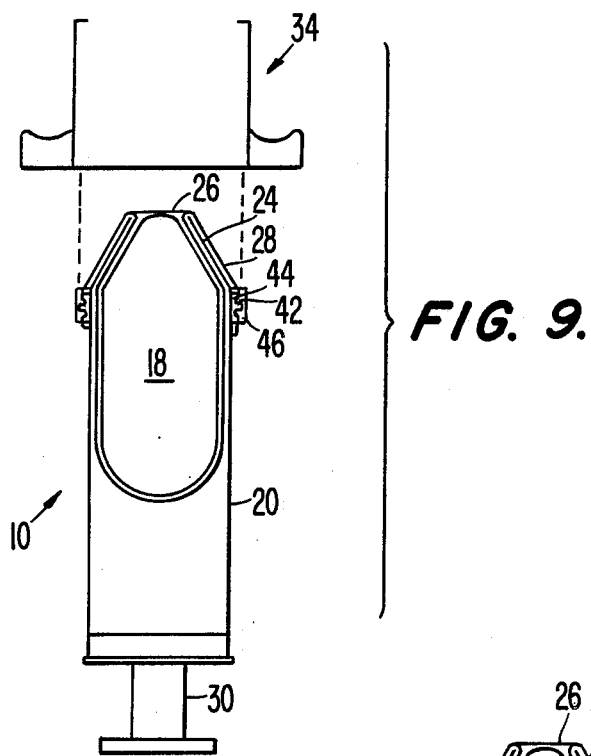
Figure 10:
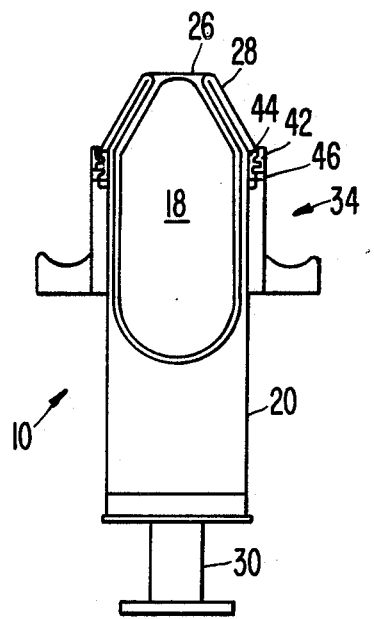
Figure 11:
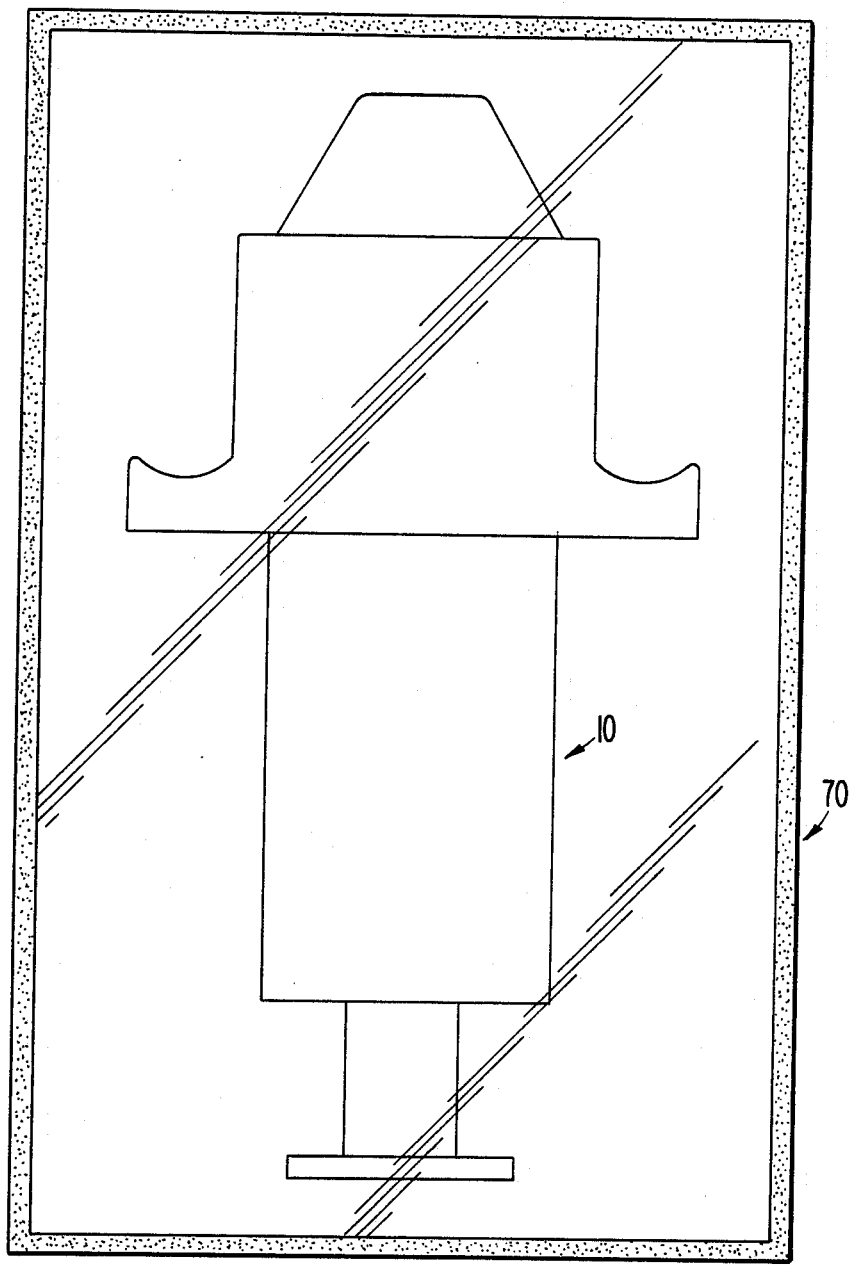

FIG. 1 is an illustration of the instant invention in use.
FIG. 2 is an illustration of a mammary prosthesis.
FIG. 3 is a sectional view of the injector taken along lines 3—3 of FIG. 1.
FIG. 4 is an enlarged view taken from FIG. 3.
FIG. 5 is a sectional view illustrating the operation of the injector.
FIG. 6 is an enlarged view taken from FIG. 5.
FIGS. 7-10 illustrate the assembly of the injector.
FIG. 11 is an illustration of an assembled injector within a plastic envelope.

DETAILED DESCRIPTION OF THE INVENTION

Referring to the drawings wherein like numerals indicate like elements there is shown in FIG. 1, an injector 10 made according to the instant invention. The injector 10 is used to insert a mammary prosthesis 18 (see FIG. 2) through an incision 12 located at the fold at the base of a breast 14 on a patient's torso 16. The surgical procedure leading up to and following the prosthesis implantation is the same as the conventional procedure, the difference from the conventional procedure is the use of the instant injector 10. Since the procedure is well known, but for the use of the injector 10, it will not be discussed herein.

FIG. 2 illustrates a mammary prosthesis 18 which is known in the art. Such prosthesises may consist of a Silastic ® bag filled with liquid silicone or a polyurethane foam. These prosthesises range in size from about 200 to about 800 cc.

Referring to FIG. 3, the injector 10 comprises a hollow cylindrical rigid walled tube 20 defining a cavity 22. Tube 20 has a truncated conical nozzle 24 at its first end and opening closed by a cap 30 at its opposite end. Nozzle 24 has an opening 26 at the truncated edge of the cone. Nozzle 24 may include a flared edge or flange 62 at the edge portion surrounding opening 26. See FIG. 6. Cap 30 is preferably releasably engagable, e.g. a friction fit or screw threads, in the tube 20 and includes a shoulder 32 upon which a thumb 60 may rest and a handle 33.

The diameter of cavity 22 and opening 26 will depend upon the volumetric size of the prosthesis and the material of construction of the prosthesis. For example, a 350 cc silicone prosthesis is easily ejected from an injector having a 2 inch diameter cavity and a 1 inch diameter opening, while a 250 cc polyurethane prosthesis is ejected with some difficulty from an injector having a 2 inch diameter cavity and a 1⅛ inch diameter opening.

A pull assembly 34 includes a tubular body 36, having an internal diameter greater than the external diameter of tube 20, with finger grips 38 located adjacent its first end and a shoulder 40 located adjacent its opposite end. Preferably, there are two finger grips 38 which are diametrically opposed on and extend radially from body 36. Each finger grip 38 may include an arcuate surface to facilitate a secure grip. Shoulder 40 is an inwardly directed circumferential flange which has an internal diameter greater than the external diameter of tube 20. Shoulder 40 must be sufficiently wide to engage the locking mechanism 41, discussed hereinafter.

A locking mechanism 41, see FIG. 4, comprises a collar 44, a front locking ring 42 and a rear locking ring 46. Collar 44 is ring shaped and includes an outwardly extending circumferential flange 48 which is located approximately equidistant the upper and lower edges of collar 44. The internal diameter of collar 44 is slightly greater than the external diameter of tube 20 to allow easy sliding of collar 44 along the external surface of tube 20, as will be explained in greater detail below. Front locking ring 42 and rear locking ring 46 have internal diameters which are sufficient to snugly fit on the collar when a bag 28 is interposed therebetween. Collar 44 also includes adjacent the upper and lower sides of flange 48 a front channel 50 and a rear channel 54. Front locking ring 42 includes a front ring flange 52 which is adapted to be received within channel 50. Rear locking ring 46 includes a rear ring flange 56 which is adapted to be received within channel 52. The assembly and operation of the pull assembly 34 and locking mechanism 41 will be discussed below.

The material of construction for the injector 10, excluding prosthesis 18 and bag 28 which are discussed elsewhere herein, are chosen depending upon whether the injector will be reuseable or disposable. If a reusable injector is chosen, the material of construction must be able to withstand repeated sterilization, e.g. stainless steel. If a disposable injector is chosen, the material of construction does not have to withstand repeated sterilizations and should be relatively inexpensive, e.g. plastic. Any plastic, for example, lexan, delrin or acrylics, may be used.

Prosthesis 18 is held within bag 28 which is inserted into cavity 22. See FIG. 3. The opened end of bag 28 is threaded through opening 26 and engages locking mechanism 41. The portion of bag 28 which engages locking mechanism 41 is placed between collar 44 and front and rear locking rings 42, 46. When the locking rings are in place on the collar, bag 28 is tightly gripped by the locking mechanism so that when the locking mechanism is slid along tube 20, bag 28 is removed from cavity 22. Bag 28 acts as a lubricant to facilitate the ejection of the prosthesis 18 from cavity 22 and through nozzle 24 and opening 26. Preferably, bag 28 is made of a material selected from the group consisting of woven nylon, woven polypropylene, woven polyester, or non-woven expanded PTFE, non-woven PTFE polyester multiply. The selection of material for bag 28 will depend upon the prosthesis and material used to construct tube 20. For example, woven nylon works well with a silicone prosthesis and a plastic tube 20.

The assembly of injector 10 is described with reference to FIGS. 7-10. Prosthesis 18 is inserted into bag 28 and then both are inserted into cavity 22 through the opened end of tube 20 which receives cap 30. The opened end of bag 28 is allowed to extend through opening 26 while the prosthesis 18 remains within the nozzle 24 and cavity 22. Collar 44 is placed on tube 20 adjacent the base of nozzle 24. See FIG. 7. Cap 30 is inserted into the opened end of tube 20. The opened end of bag 28 is pulled over nozzle 24 and collar 44. Front and rear locking rings are slid over collar 44 and abut in place against flange 48 of collar 44. See FIG. 8. Pull assembly 34 is then slid over locking assembly 41 (see FIG. 9) and the injector is ready to use (see FIG. 10).

In operation, the surgeon holds the injector 10 by gripping finger grips 38 with his forefingers 58 and resting his thumbs 30 on shoulder 32 of cap 30. See FIG. 1. The opening 26 of nozzle 24 of the assembled injector 10 (e.g. FIGS. 3 or 10) is inserted into incision 12. Thereafter, the surgeon pulls finger grips 38 toward cap 30, thereby pulling bag 28 along with prosthesis 18 out through opening 26. See FIG. 5. The bag 28 is pulled along the exterior surface of the nozzle 24 and tube 20; while prosthesis 18 is passed through incision 12. Once the prosthesis is completely out of the injector, the injector is set aside.

With regard to the mechanism for ejecting the prosthesis from the injector, a manual method is discussed above, however, a pneumatic mechanism may also be used.

The injector 10, when in a disposable form, may be preloaded with a prosthesis and then aseptically sealed within a plastic envelope 70. See FIG. 11. Thus the injector and prosthesis are delivered to the operating sterile field in sterile form ready for use.

The present invention may be embodied in other specific forms without departing from the spirit or essential attributes thereof and, accordingly, reference should be made to the appended claims, rather than to the foregoing specifications, as indicating the scope of the invention.

We claim:

1. A mammary prosthesis injector comprising:
    a hollow rigid walled tube having an opening at one end of said tube, said tube including inner and outer surfaces and sized to receive an implantable mammary prosthesis;
    friction reducing means for reducing friction between the inner surface said hollow tube and the prosthesis, said friction reducing means including a bag at least partially located within said tube and interposed between the inner surface and mammary prosthesis, said bag sized to accommodate the mammary prosthesis within the hollow tube, and to reduce friction between said inner surface of said tube and the mammary prosthesis; and
    means operatively coupled to said tube for injecting the prosthesis through said opening from within said tube.

2. A mammary prosthesis injector for implanting a mammary prosthesis into a patient comprising:
    a hollow tube including an opening at one end thereof and having outer and inner surfaces;
    a bag made of a biocompatible material at least partially, within said tube and having one end extending outwardly of said opening, said bag adapted to hold a mammary prosthesis in the hollow tube and to reduce friction between said inner surface of the tube and the prosthesis;
    a pulling means slidably mounted on said outer surface of the tube and coupled to said one end of the bag;
    whereby said mammary prosthesis is ejected from the tube and through the opening as said pulling means is slid along the outer surface of the tube.

3. The injector according to claim 2, wherein said means for injecting comprises:
    a slidable body having two open ends and having an inwardly extending flange adjacent the opening at one of said ends; and
    locking means for locking said bag slidably mounted upon said tube between said tube and said slidable tubular body and engaging said flange.

4. The injector according to claim 2, wherein said locking means comprises:
    an annular collar having an outwardly extending circumferential flange;
    first locking and second locking rings disposed on either side of said circumferential flange;
    whereby the collar is slidably disposed on said outer surface of the tube and said one end of the bag is placed over the circumferential flange and intermediate said collar and locking rings thereby securing the bag to said collar.

5. The injector according to claim 2, wherein said locking means further comprises outwardly extending finger grip means.

6. The mammary prosthesis injector according to claim 1 wherein said means for injecting comprises locking means for locking said friction reducing means in sliding engagement with said tube and pulling means for pulling said locking means along said tube.

7. The injector according to claim 1, wherein said opening defines a truncated conical nozzle.

8. The injector according to claim 7 wherein said bag is made of a material selected from the group consisting of woven nylon, woven polypropylene, woven polyester, non-woven expanded PTFE, non-woven PTFE polyester multiply.

9. The injector according to claim 7 further comprising a flared edge located at an edge portion of said opening of said tube.

10. The injector according to claim 7, wherein said opening defines a truncated conical nozzle.

11. The injector according to claim 7, further comprising an end cap configured to be attached to the end of the tube opposite said opening.

12. A mammary prosthesis injector system for implanting a mammary prosthesis into a patient comprising:
 a mammary prosthesis;
 a hollow tube including an opening at one end thereof and having inner and outer surfaces;
 a biocompatible bag disposed, at least partially, within said tube and having one end extending outwardly of said opening, said bag adapted to hold said prosthesis in the hollow tube and to reduce friction between said inner surface of the tube and the prosthesis;
 a pulling means slidably mounted on said outer surface of the tube and coupled to said one end of the bag;
 whereby said mammary prosthesis is ejected from the tube and through the opening as said pulling means is slid along the outer surface of the tube.

13. The injector according to claim 12 further comprising a mammary prosthesis located within said hollow tube.

14. The injector according to claim 12 further comprising a sealed envelope enclosing said injector.

* * * * *